United States Patent
Nelson et al.

(10) Patent No.: US 11,730,373 B2
(45) Date of Patent: Aug. 22, 2023

(54) SENSOR WITH VARIABLE DEPTH INTERROGATION

(71) Applicant: Covidien LP, Mansfield, MA (US)

(72) Inventors: Christopher S. Nelson, Longmont, CO (US); Ulf Borg, Mead, CO (US)

(73) Assignee: Covidien LP, Mansfield, MA (US)

( * ) Notice: Subject to any disclaimer, the term of this patent is extended or adjusted under 35 U.S.C. 154(b) by 491 days.

(21) Appl. No.: 16/853,100

(22) Filed: Apr. 20, 2020

(65) Prior Publication Data

US 2021/0321871 A1    Oct. 21, 2021

(51) Int. Cl.
*A61B 5/00*      (2006.01)
*A61B 5/1455*    (2006.01)

(52) U.S. Cl.
CPC ........ *A61B 5/0082* (2013.01); *A61B 5/14552* (2013.01); *A61B 5/14553* (2013.01); *A61B 2503/045* (2013.01); *A61B 2562/0238* (2013.01); *A61B 2562/0242* (2013.01); *A61B 2562/04* (2013.01); *A61B 2562/164* (2013.01)

(58) Field of Classification Search
CPC .............. A61B 5/1455; A61B 5/14552; A61B 5/14553; A61B 2562/0238; A61B 2562/0243; A61B 2562/04; A61B 2562/164; A61B 2562/0242
See application file for complete search history.

(56) References Cited

U.S. PATENT DOCUMENTS

| | | | |
|---|---|---|---|
| 5,465,714 A | 11/1995 | Scheuing | |
| 6,416,471 B1 * | 7/2002 | Kumar | A61B 5/0022 128/903 |
| 6,690,958 B1 | 2/2004 | Walker et al. | |
| 7,120,481 B2 * | 10/2006 | Keller | A61B 5/14553 600/339 |
| 9,226,703 B2 * | 1/2016 | Inoue | A61B 5/14553 |
| 2005/0033130 A1 * | 2/2005 | Rall | A61B 5/1464 600/338 |

(Continued)

FOREIGN PATENT DOCUMENTS

| | | |
|---|---|---|
| EP | 1374778 A1 | 1/2004 |
| EP | 2106745 A1 | 10/2009 |

(Continued)

OTHER PUBLICATIONS

International Application No. PCT/US2021/026311 International Search Report and Written Opinion dated Jul. 2, 2021, 14 pages.

*Primary Examiner* — Eric F Winakur
(74) *Attorney, Agent, or Firm* — Shumaker & Sieffert, P.A.

(57) ABSTRACT

A sensor for evaluating tissue of a subject is provided. The sensor includes a flexible spine disposable on the subject, a flexible member that includes first and second flexible member portions accommodated within the flexible spine, a light source, a detector and a rigid member. The light source is attached to the first flexible member portion and is configured to emit light toward the tissue. The detector is attached to the second flexible member portion and is configured to receive the light having reflected off the tissue. The rigid member is coupled with the first and second flexible member portions. In response to a curvature of the flexible spine, the rigid member moves the first and second flexible member portions along the flexible spine to adjust a distance between the light source and the detector.

6 Claims, 3 Drawing Sheets

(56) References Cited

U.S. PATENT DOCUMENTS

2008/0316488 A1    12/2008   Mao et al.
2009/0088619 A1     4/2009   Turner et al.
2017/0367650 A1    12/2017   Wallois et al.
2018/0360327 A1    12/2018   Duval et al.

FOREIGN PATENT DOCUMENTS

EP         3226200 A1   10/2017
WO    2012051617 A2    4/2012

* cited by examiner

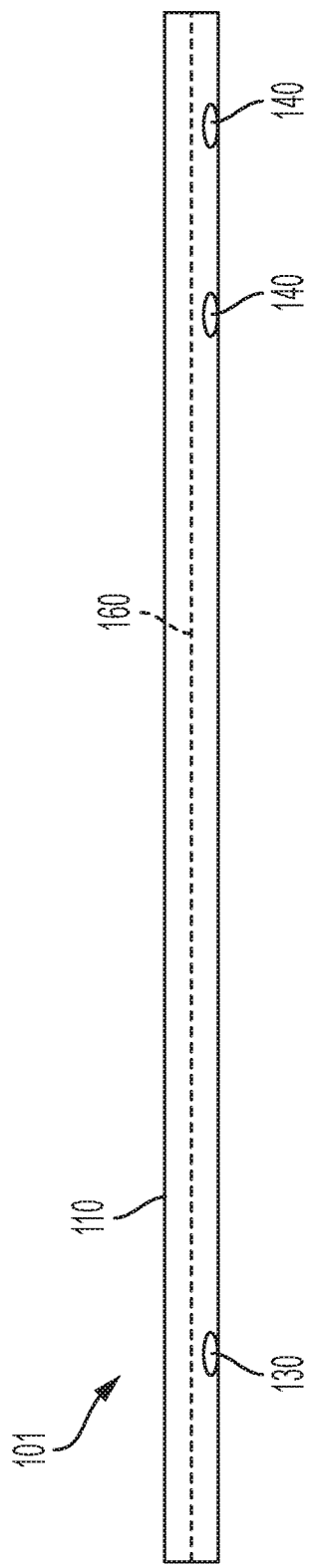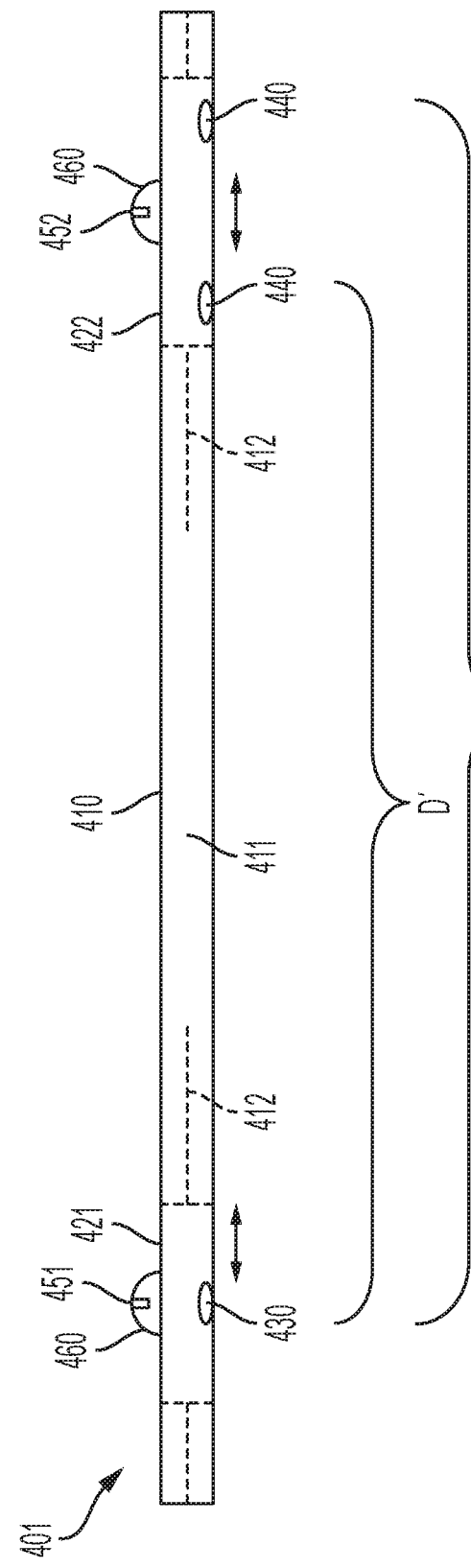

SENSOR WITH VARIABLE DEPTH INTERROGATION

FIELD

The present technology is generally related to sensors with variable depth interrogation capability.

BACKGROUND

Present day rSO2 sensors typically utilize near-infrared spectroscopy (NIRS), which is a spectroscopic method that uses the near-infrared region of the electromagnetic spectrum (i.e., from about 780 nm to about 2,500 nm), and operate by emitting light from emitters toward tissue to be interrogated. The emitters can be provided as light emitting diodes (LEDs) and the light from the emitters penetrates the tissue to be interrogated and then reflects back toward detectors. These rSO2 sensors often have a characteristic depth of light penetration and lead to the rSO2 sensors failing to interrogate intended tissues.

The characteristic depth of light penetration can result from various factors. These include, but are not limited to, the fact that there is often a fixed distance between the emitters and the detectors and the fact that there is usually a fixed level of power that is supplied to the emitters.

With rSO2 sensors having the characteristic depth of light penetration, curvatures of surfaces to which rSO2 sensors can be attached determine an angle between the actual tissue to be interrogated and the emitters and the detectors of the rSO2 sensors. For example, a premature baby will have a head with a greater curvature (at location of an rSO2 sensor) than an adult and this greater curvature will cause an increasingly shallow angle for the emitters and the detectors. This will in turn lead to an interrogation of tissue by a given rSO2 sensor at more shallow depths for the premature baby than the adult. By contrast, the adult's head will have a flatter shape that will contribute to interrogation of tissue at a greater depth by the given rSO2 sensor.

As an additional consideration, there are cases in which there are tissues where a shallow interrogation is preferred but the angle of the emitters and the detectors of a given rSO2 sensor is set for deeper penetration. In such cases, the power supplied to the emitters, which is typically fixed, can tend to be excessive.

SUMMARY

The techniques of this disclosure generally relate sensors with variable depth interrogation capability.

In one aspect, the present disclosure provides a sensor for evaluating tissue of a subject is provided. The sensor includes a flexible spine disposable on the subject, a flexible member that includes first and second flexible member portions accommodated within the flexible spine, a light source, a detector and a rigid member. The light source is attached to the first flexible member portion and is configured to emit light toward the tissue. The detector is attached to the second flexible member portion and is configured to receive the light having reflected off the tissue. The rigid member is coupled with the first and second flexible member portions. In response to a curvature of the flexible spine, the rigid member moves the first and second flexible member portions along the flexible spine to adjust a distance between the light source and the detector.

In another aspect, the disclosure provides a sensor for evaluating tissue of a subject is provided. The sensor includes a flexible spine disposable on the subject, first and second members which are slidable along the flexible spine, a light source and a detector attached to and slidable with the first and second members, respectively, the light source being configured to emit light toward the tissue and the detector being configured to receive the light having reflected off the tissue, and first and second locking elements configured to constrain, lock or adhere the first and second members in place along the flexible spine, respectively.

In another aspect, the disclosure provides a sensor for evaluating tissue of a subject is provided. The sensor includes a flexible spine disposable on the subject, a light source affixed to the flexible spine and configured to emit light toward the tissue, a detector affixed to the flexible spine and configured to receive the light having reflected off the tissue and a gage coupled to the flexible spine and configured to indicate an operational condition of the light source and the detector in accordance with a curvature of the flexible spine.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 3 is a side schematic illustration of a sensor with a flexible circuit embedded therein in accordance with embodiments;

FIG. 4 is a side schematic illustration of a sensor with a manually movable light source and a manually movable detector in accordance with embodiments;

DETAILED DESCRIPTION

As will be described below, an rSO2 sensor is provided and includes an emitter and a detector. The rSO2 sensors has a variable emitter power level and a variable displacement between the emitter and the detector to thereby achieve an appropriate depth of interrogation with a corresponding angle at which light from the emitter is reflected back to the detector. The rSO2 sensor further includes a self-adjusting capability.

Figure 1:
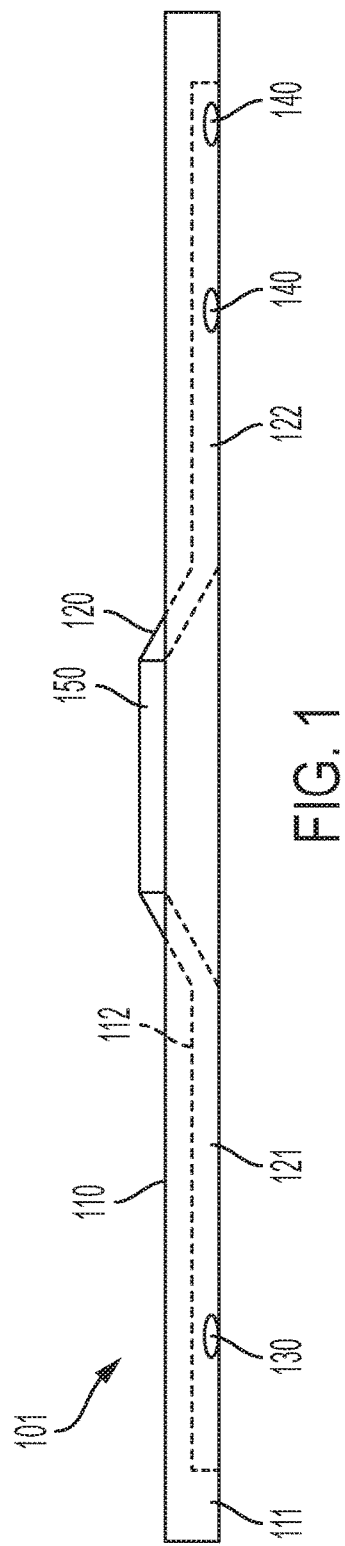
FIG. 1 is a side schematic illustration of a sensor with flexible member portions and a rigid member in accordance with embodiments.
Figure 2:
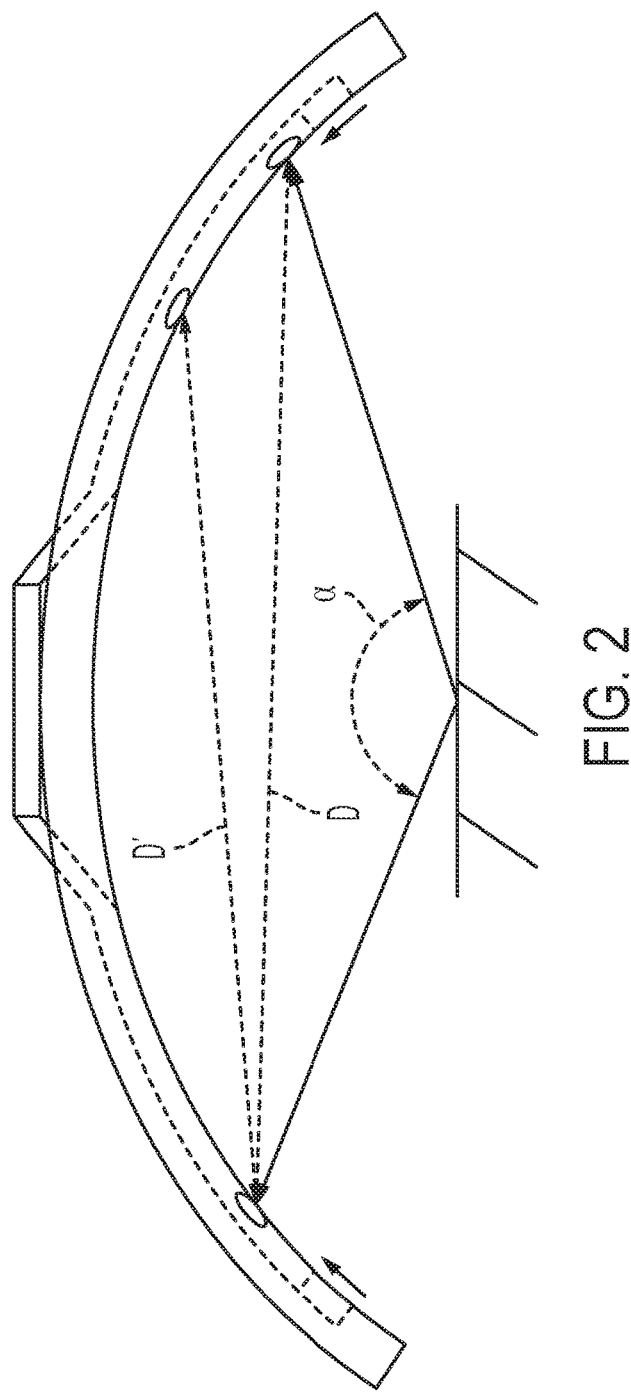
FIG. 2 is a side schematic illustration of the sensor of FIG. 1 in a curved condition.

With reference to FIGS. 1 and 2, a sensor 101 is provided for use in evaluating tissue (i.e., tissue to be interrogated) of a subject. The subject can be a portion of a patient's body, for example, such as a skull of a baby with a relatively large curvature or radius of curvature or a skull of an adult with a relatively small curvature or radius of curvature.

The sensor 101 includes a flexible spine 110 that is disposable on the subject, a flexible member 120, a light source 130, a detector 140 and a rigid member 150. The flexible spine 110 includes an elongate body 111 that is configured to curve along a curvature of the subject and that is formed to define an internal cavity 112. The flexible member 120 includes a first flexible member portion 121 that can be accommodated and slidable within a corresponding portion of the internal cavity 112 of the flexible spine 110 and a second flexible member portion 122 that can be accommodated and slidable within a corresponding portion of the internal cavity 112 of the flexible spine 110. The light source 130 can be provided as one or more light sources 130 attached to the first flexible member portion 121 of the flexible member 120. Each of the one or more light sources 130 can include or be provided as an LED and is configured to emit light toward the tissue. The detector 140 can be provided as one or more detectors 140 attached to the second flexible member portions 122. Each of the one or more detectors 140 can include or be provided as a photodetector and is configured to receive the light having reflected off the tissue. The rigid member 150 is coupled at opposite ends thereof with the first flexible member portion 121 and with the second flexible member portion 122. In this way, in response to a curvature of the flexible spine 110 (i.e., resulting from the flexible spine 110 being disposed in abutment with the subject), the rigid member 150 moves the first and second flexible member portions 121 and 122 along the flexible spine 110 to adjust distances D, D' (see FIG. 2) between the one or more light sources 130 and the one or more detectors 140.

While one or more light sources 130 can be attached to the first flexible member portion 121 and one or more detectors 140 can be attached to the second flexible member portion 122, the present description relates to the exemplary case of a single light source 130 being attached to the first flexible member portion 121 and two detectors 140 being attached to the second flexible member portion 122 as shown in FIGS. 1 and 2. This is being done for purposes of clarity and brevity and should not be interpreted as limiting of the overall scope of the disclosure in any way.

With the construction described above, an angle of reflection a that is formed between the light emitted from the light source 130 and the light incident on the detectors 140 is increased due to the movement of the first and second flexible member portions 121 and 122 along the flexible spine 110 and the corresponding adjustment of the distances D, D' between the light source 130 and the detectors 140. This increased angle of reflection a results in an improved performance of the detectors 140 and the sensor 101 as a whole (as compared to a performance capability of the detectors 140 with a relatively shallow angle of reflection as found in conventional sensors).

With continued reference to FIGS. 1 and 2 and with additional reference to FIG. 3, at least one or both of a power of the light source 130 and a sensitivity of each of the detectors 140 can be variable and can be controllable by an operator and/or automatically controllable to optimize a performance of the sensor 101. In the former case, an operator can adjust the power of the light source 130 to insure that the light emitted from the light source 130 has sufficient strength or intensity to penetrate to the tissue and then to reflect off the tissue with sufficient strength or intensity to reach the detectors 140. Similarly, in the former case, the operator can adjust the sensitivity of the detectors 140 to insure that they are sufficiently sensitive to properly receive and register the reflected light. Conversely, as shown in FIG. 3, the sensor 101 can further include a flexible circuit 160 embedded in the flexible spine 110 and disposed in electrical communication with at least one of the light source 130 and the detectors 140. In these or other cases, as the flexible spine 110 curves or flexes, a resistance of the flexible circuit 160 increases. This increased resistance can be read by corresponding circuitry in the sensor 101 and can be interpreted by a monitoring algorithm or internal logic as an indicator of the curvature or flexion of the flexible spine 110. The monitoring algorithm or logic can then control the at least one of the power of the light source 130 and the sensitivity of each of the detectors 140.

With reference to FIG. 4, a sensor 401 is provided for use in evaluating tissue (i.e., tissue to be interrogated) of a subject. The subject can be a portion of a patient's body, for example, such as a skull of a baby with a relatively large curvature or radius of curvature or a skull of an adult with a relatively small curvature or radius of curvature.

The sensor 401 includes a flexible spine 410 that is disposable on the subject, a first member 421, a second member 422, a light source 430, a detector 440 and first and second locking elements 451 and 452. The flexible spine 410 includes an elongate body 411 that is configured to curve along a curvature of the subject and that is formed to define an internal track 412. The first member 421 and the second member 422 are each slidable along the internal track 412 of the flexible spine 410. The light source 430 can be provided as one or more light sources 430 attached to the first member 421. Each of the one or more light sources 430 can include or be provided as an LED and is configured to emit light toward the tissue. The detector 440 can be provided as one or more detectors 440 attached to the second member 422. Each of the one or more detectors 440 can include or be provided as a photodetector and is configured to receive the light having reflected off the tissue. The sliding of the first member 421 and the second member 422 along the internal track 412 of the flexible spine 410 serves to adjust distances D, D' between the one or more light sources 430 and the one or more detectors 440. The first and second locking elements 451 and 452 are configured to constrain, lock or adhere the first and second members 421 and 422 in place along the internal track 412 of the flexible spine 410, respectively. Each of the first and second members 421 and 422 can further include a gripping tab 460 that can be gripped by an operator to facilitate the sliding of the first and second members 421 and 422. Each gripping tab 460 can be engageable with a corresponding one of the first and second locking elements 451 and 452 (e.g., by the corresponding one of the first and second locking elements 451 and 452 being provided as a foldable tab that can be folded into a notch formed in the gripping tab 460).

While one or more light sources 430 can be attached to the first member 421 and one or more detectors 440 can be attached to the second member portion 422, the present description relates to the exemplary case of a single light source 430 being attached to the first member 421 and two detectors 440 being attached to the second member 422 as shown in FIG. 4. This is being done for purposes of clarity and brevity and should not be interpreted as limiting of the overall scope of the disclosure in any way.

With the construction described above, an angle of reflection a (see FIG. 2) that is formed between the light emitted from the light source 430 and the light incident on the detectors 440 is increased due to the sliding of the first and second members 421 and 422 along the internal track 412 of the flexible spine 410 and the corresponding adjustment of the distances D, D' between the light source 430 and the detectors 440. This increased angle of reflection a results in an improved performance of the detectors 440 and the sensor 401 as a whole (as compared to a performance capability of the detectors 440 with a relatively shallow angle of reflection as found in conventional sensors).

With continued reference to FIG. 4 and with reference back to FIG. 3, at least one or both of a power of the light source 430 and a sensitivity of each of the detectors 440 can be variable and can be controllable by an operator and/or automatically controllable to optimize a performance of the sensor 401 as described above.

Figure 5:
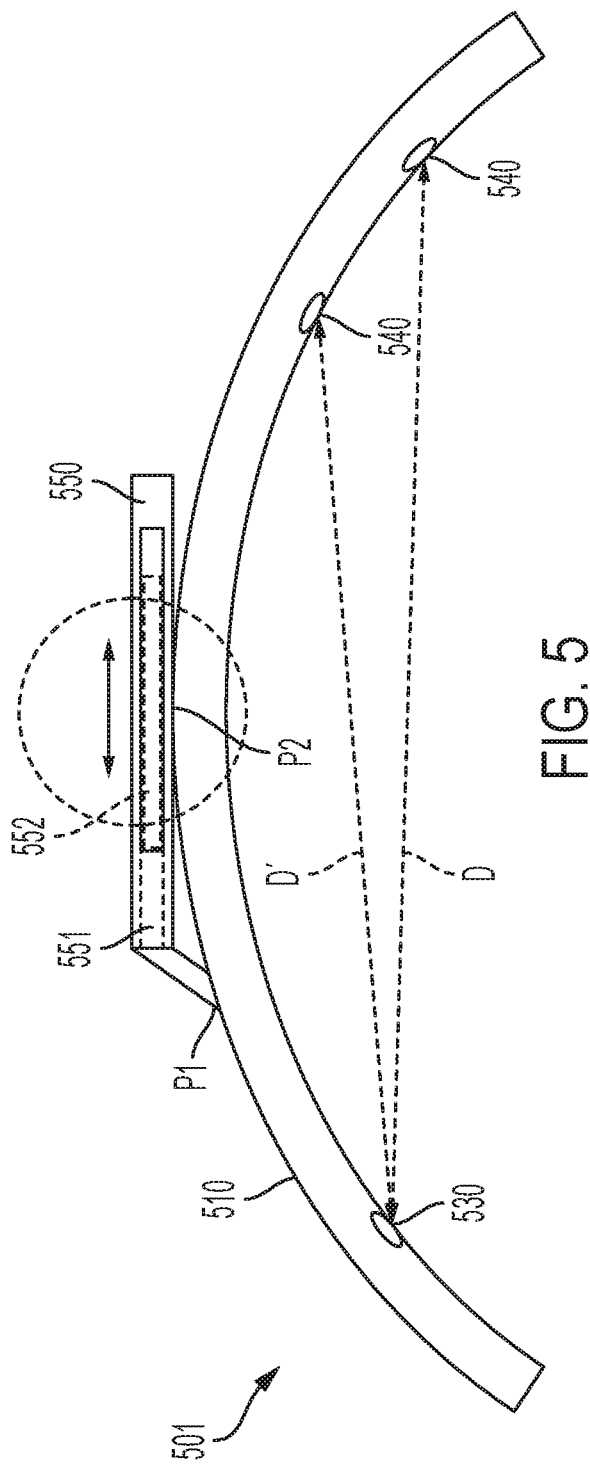
FIG. 5 is a side schematic illustration of a sensor with a gage in accordance with embodiments.
Figure 6:
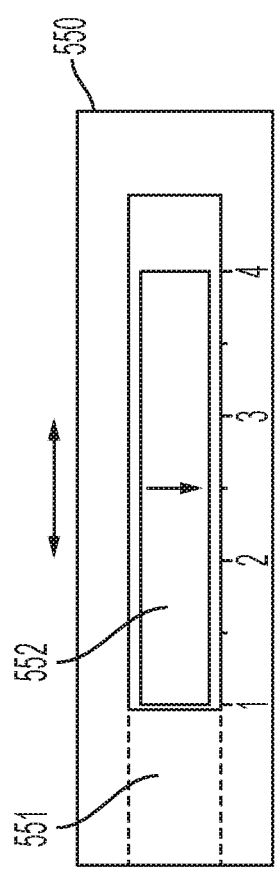
FIG. 6 is top schematic illustration of the gage of FIG. 5 in accordance with embodiments.

With reference to FIGS. 5 and 6, a sensor 501 is provided for use in evaluating tissue (i.e., tissue to be interrogated) of a subject. As above, the subject can be a portion of a patient's body, for example, such as a skull of a baby with a relatively large curvature or radius of curvature or a skull of an adult with a relatively small curvature or radius of curvature.

The sensor 501 includes a flexible spine 510 that is disposable on the subject, a light source 530, a detector 540 and a gage 550. The flexible spine 510 includes an elongate body 511 that is configured to curve along a curvature of the subject. The light source 530 can be provided as one or more light sources 530 affixed to the flexible spine 510. Each of the one or more light sources 530 can include or be provided as an LED and is configured to emit light toward the tissue. The detector 540 can be provided as one or more detectors 540 affixed to the flexible member 510. Each of the one or more detectors 540 can include or be provided as a photodetector and is configured to receive the light having reflected off the tissue. The gage 550 is coupled to the flexible spine 510 and is configured to indicate an operational condition of the one or more light sources 530 and the one or more detectors 540 in accordance with a curvature of the flexible spine 510.

While one or more light sources 530 and one or more detectors 540 can be affixed to the flexible spine 510, the present description relates to the exemplary case of a single light source 530 and two detectors 540 being affixed to the flexible spine 510 as shown in FIG. 5. This is being done for purposes of clarity and brevity and should not be interpreted as limiting of the overall scope of the disclosure in any way.

With continued reference to FIGS. 5 and 6 and with reference back to FIG. 3, at least one or both of a power of the light source 530 and a sensitivity of each of the detectors 540 can be variable and can be controllable by an operator and/or automatically controllable to optimize a performance of the sensor 501 as described above.

The gage 550 can include a rigid member 551 that is affixed to a fixed point P1 of the flexible spine 510 and a sliding gage 552 that is affixed to the flexible spine 510 at an attachment point P2 and is slidable along the rigid member 551 to be indicative of the operational condition. In accordance with embodiments, the operational condition can include an optimal penetration depth of the light emitted from the light source 530 into the tissue.

Technical effects and benefits of the intelligent architecture are the provision of an improved sensor that is usable in, for example, non-invasive patient monitoring that requires light penetration to interrogate tissue at a desired depth. The improved sensor can be used on various parts of a body (i.e., somatic sites) and accommodates different body types. The improved sensor alleviates a need for multiple sensors having varying displacements between light sources and detectors.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A sensor for evaluating tissue of a subject and comprising:
    a flexible spine disposable on the subject;
    a flexible member comprising first and second flexible member portions accommodated within the flexible spine;
    a light source and a detector attached to the first and second flexible member portions, respectively, the light source being configured to emit light toward the tissue and the detector being configured to receive the light having reflected off the tissue; and
    a rigid member coupled with the first and second flexible member portions, wherein, in response to a change in curvature of the flexible spine, the rigid member moves the first and second flexible member portions relative to the flexible spine to adjust a distance between the light source and the detector.

2. The sensor according to claim 1, wherein the flexible spine comprises an elongate body configured to curve along a curvature of the subject and formed to define an internal cavity in which the flexible member is slidable.

3. The sensor according to claim 1, wherein one or more light sources and one or more detectors are attached to the first and second flexible member portions, respectively.

4. The sensor according to claim 1, wherein at least one of a power of the light source and a sensitivity of the detector is variable and controllable by an operator.

5. The sensor according to claim 1, wherein at least one of a power of the light source and a sensitivity of the detector is variable and automatically controllable.

6. The sensor according to claim 5, further comprising a flexible circuit embedded within the flexible spine and disposed in electrical communication with at least one of the light source and the detector.

* * * * *